United States Patent
Maki et al.

(10) Patent No.: US 6,579,260 B2
(45) Date of Patent: Jun. 17, 2003

(54) BALLOON FOR MEDICAL TUBE AND MEDICAL TUBE EQUIPPED WITH THE SAME

(75) Inventors: Shin Maki, Kanagawa-ken (JP); Shigeki Ariura, Kanagawa-ken (JP); Shigenobu Iwahashi, Kanagawa-ken (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/855,709

(22) Filed: May 16, 2001

(65) Prior Publication Data

US 2001/0044597 A1 Nov. 22, 2001

Related U.S. Application Data (62) Division of application No. 09/059,402, filed on Apr. 14, 1998, now Pat. No. 6,261,260.

(30) Foreign Application Priority Data

Apr. 15, 1997 (JP) ............................................... 9-97082
Apr. 15, 1997 (JP) ............................................... 9-97084

(51) Int. Cl.$^7$ ............................................ A61M 29/00
(52) U.S. Cl. ................................. 604/103.07; 604/96.01
(58) Field of Search ........................ 604/103.07, 96.01, 604/99, 915, 916, 101.01, 919, 103.06, 103.08; 428/34.3, 35.5, 36.9

(56) References Cited

U.S. PATENT DOCUMENTS

| | | | |
|---|---|---|---|
| 3,811,448 A | | 5/1974 | Morton |
| 4,040,413 A | | 8/1977 | Ohshiro |
| 4,083,369 A | | 4/1978 | Sinnreich |
| 4,456,000 A | | 6/1984 | Schjeldahl et al. |
| 4,581,017 A | * | 4/1986 | Sahota ...................... 604/101 |
| 4,771,776 A | * | 9/1988 | Powell et al. ............... 128/344 |
| 5,116,305 A | | 5/1992 | Milder et al. |
| 5,397,307 A | | 3/1995 | Goodin |
| 5,447,152 A | | 9/1995 | Kohsai et al. |
| 5,868,704 A | * | 2/1999 | Campbell et al. ............. 604/96 |
| 5,954,740 A | * | 9/1999 | Ravenscroft et al. ........ 606/194 |
| 6,099,497 A | * | 8/2000 | Adams et al. ............. 604/96.01 |
| 6,110,192 A | * | 8/2000 | Ravenscroft et al. ........ 606/194 |

FOREIGN PATENT DOCUMENTS

| | | |
|---|---|---|
| EP | 0 669 163 | 8/1995 |
| EP | 0 737 488 | 10/1996 |
| FR | 2 738 489 | 3/1997 |
| JP | 8-47539 | 2/1996 |
| JP | 8-57035 | 3/1996 |

* cited by examiner

*Primary Examiner*—Sharon Kennedy
(74) *Attorney, Agent, or Firm*—Burns, Doane, Swecker & Mathis, LLP (57) ABSTRACT

A cylindrical balloon for medical tubes, which is susceptible to bending operations, comprises a low stretchable section formed, by a partial cross-linking treatment, on the balloon along the circumferential direction thereof. A medical tube equipped with a balloon comprises a shaft tube for being inserted into a living body, a cylindrical balloon liquid-tightly connected to the shaft tube at the periphery on the tip thereof, a first lumen which is formed within the shaft tube and which communicates with the interior of the balloon, and at least one second lumen which is formed within the shaft tube and which is opened at the tip of the shaft tube; or comprises a shaft tube which is inserted into a living body, a cylindrical balloon, one end of which is liquid-tightly connected to the shaft tube at the tip thereof, a long tool for medical treatments or for diagnoses, whose tip portion is liquid-tightly connected to the other end of the balloon directly or indirectly, and a lumen which is formed within the shaft tube and communicates with the interior of the balloon so that a liquid can pass through the balloon and which accommodates the long tool for medical treatments or for diagnoses, wherein the cylindrical balloon is the same as that defined above.

24 Claims, 4 Drawing Sheets

BALLOON FOR MEDICAL TUBE AND MEDICAL TUBE EQUIPPED WITH THE SAME

This application is a divisional of application Ser. No. 09/059,402, filed on Apr. 14, 1998, now U.S. Pat. No. 6,261,260, issued Jul. 17, 2001.

BACKGROUND OF THE INVENTION (a) Field of the Invention

The present invention relates to a balloon for medical tubes and a medical tube equipped with such a balloon. More specifically, the present invention pertains to a balloon for medical tubes, which has variable bendability, which can impart, to a medical tube to be inserted into a living body for examinations and/or treatments, a direction-selecting function (the ability to select the course or direction of the tip of the medical tube) due to the variable or arbitrary bendability of the balloon or can impart, to the medical tube, a function of separating tissues by the variable bending motions of the balloon, while making the most use of the difference in the partial stretchability of the balloon induced when a pressurized fluid is injected therein, as well as a medical tube equipped with such a balloon.

(b) Description of the Prior Art

Operations performed in the past requiring severe operative invasion has gradually been superseded by the operative techniques with less operative invasion. For instance, there have spectacularly been spread widely therapeutic methods with minimum invasion therapy (MIT), mainly based on techniques which make use of catheters and endoscopes, such as PTCA, PTA and stent techniques, atelectomy, embolization and operations performed under an endoscope.

In particular, in the field of the catheter techniques, there have been developed a variety of balloon-catheters in order to, for instance, supply a medical fluid or an infusion solution to a specific site in a body cavity such as a blood vessel, a digestive tract, a uterine tube or a ureter, or to expand a site with a stenosis by the expansive force of a balloon.

However, a higher operative technique will require the development of a catheter whose tip portion has an ability to select its course of advancement by the bending of the same. In respect of the bending mechanism of the tip of a catheter, various structures have been proposed, but they are all complicated and the diameter of the catheters would inevitably be increased.

In addition, a catheter has conventionally been used only for the body cavities, except for a part of operations performed under endoscopes. However, there has been desired for the development of a catheter technique which is not limited only to the transluminal approach techniques which make use of biological tracts and/or cavities such as blood vessels, as the area of catheter application is widely expanded.

A cavity should be formed within a variety of tissues by a less frictional means to treat a target site by letting a catheter arrive at a desired site from the exterior of a biological tract or cavity, unlike the technique which makes use of the biological tract or cavity. To this end, tissues should often be separated over a wide area. After the catheter arrives at the desired portion, various tools may be adapted to carry out diagnosis and/or treatments through the use of the multiple lumens of the catheter.

As a method for separating tissues, the tip of a catheter may continuously be deformed and moved after the catheter arrives at the desired site on the tissue to be separated. Various structures have been proposed, as the bending mechanisms of the tip of the catheter, but all of them are very complicated and the diameter of the catheters would inevitably be increased. Moreover, there has not yet been developed any multifunctional catheter designed from the viewpoint of the non-transluminal approach to the tissue separation from the outside of the biological tract or cavity.

SUMMARY OF THE INVENTION

The present invention has been developed to solve the foregoing various problems associated with the conventional techniques and accordingly, an object of the present invention is to provide a balloon for medical tubes, which has variable bendability, which can impart a direction-selecting function due to the variable bendability of the balloon to a medical tube inserted into a living body for examinations and/or treatments, while making the most use of the difference in partial stretchability of the balloon induced when a pressurized fluid is injected therein, which has a simple structure and whose diameter can substantially be reduced, as well as a medical tube equipped with such a balloon.

Another object of the present invention is to provide a medical tubular structure equipped with a balloon designed from the viewpoint of the non-transluminal approach to the tissue separation from the outside of the biological tract or cavity, which thus has a function for separating biological tissues by the variable ability of the balloon to undergo bending motions, which has a simple structure and whose diameter can be reduced.

The inventors of this invention have conducted various studies to achieve the aforementioned objects and have found that variable bending ability can be imparted to a balloon and a direction-selecting function can thus be imparted thereto. In other words, a low stretchable section is partially formed on a cylindrical balloon along its circumferential direction by a cross-linking treatment to thus ensure a partial difference in the stretchability of the balloon. Accordingly, the balloon can expand to a large extent on the side of the high stretchable section, while the balloon on the side of the low stretchable section can expand to a lesser extent, when a pressurized fluid is injected therein. Thus, the balloon undergoes bending towards the side of the low stretchable section and the degree of the bending can be controlled by appropriately adjusting the pressure of the pressurized fluid. Accordingly, the inventors have completed an aspect of the present invention on the basis of the foregoing findings.

Alternatively, the inventors have also found the following. A cylindrical balloon is partially subjected to a cross-linking treatment to thus form at least two low stretchable sections over less than a half of the circumferential region on the cylindrical balloon, which partially extends in the axial direction of the balloon, these sections having low stretchability are arranged in such a manner that the positions thereof are deviated from one another in the axial direction of the balloon, preferably these sections substantially do not overlap with each other in the axial direction of the balloon, and they are arranged in the opposite circumferential directions of the balloon. Thus, the balloon can expand to a large extent on the side of the high stretchable section, while the balloon on the side of the low stretchable section can expand to a lesser extent, when a pressurized fluid is injected therein. Accordingly, the balloon undergoes bending in an S-shaped form, towards the side of the low stretchable section and the degree of the bending can be controlled by appropriately adjusting the pressure of the pressurized fluid. Accordingly, an ability of variable bending motions can be imparted to the balloon by applying a pulsative pressure of a pressurized fluid to the balloon and a tissue-separating function can thus be imparted thereto. Accordingly, the inventors have likewise completed another aspect of the present invention.

According to an aspect of the present invention, there is provided a cylindrical balloon for medical tubes, which has an ability to bend and which comprises a section having low stretchability (low stretchable section) partially formed, by a cross-linking treatment, on the balloon along the circumferential direction thereof.

In the balloon for medical tubes according to preferred embodiment of the present invention, the low stretchable section which is formed by a partial cross-linking treatment extends, over less than a half of the circumferential region on the cylindrical balloon, along the axial direction thereof; or a first low stretchable section which is formed by a partial cross-linking treatment partially extends, over less than a half of the circumferential region on the cylindrical balloon, along the axial direction thereof, while a second low stretchable section which is formed by a partial cross-linking treatment partially extends, over less than a half of the circumferential region on the cylindrical balloon, along the axial direction thereof, and the first and second low stretchable sections are circumferentially arranged in opposite directions of the balloon and are also arranged in such a manner that the positions thereof are deviated from one another in the axial direction of the balloon. However, the arrangement of these low stretchable sections is not limited to the foregoing embodiments or patterns. For instance, the sections may helically extend in the axial direction of the balloon or extend at an angle with respect to the axial direction of the balloon, or further at least three such sections may be arranged alternately and oppositely along the circumferential direction of the balloon.

According to another aspect of the present invention, there is also provided a medical tube equipped with a balloon, which comprises:

a shaft tube for being inserted into a living body;
a cylindrical balloon liquid-tightly connected to the shaft tube at the periphery of the tip thereof;
a first lumen which is provided within the shaft tube and communicates with the interior of the balloon; and
at least one second lumen which is formed within the shaft tube and is opened at the tip thereof;
wherein the cylindrical balloon comprises a low stretchable section which is partially formed on the circumferential region on the balloon by a cross-linking treatment.

In this respect, the foregoing cylindrical balloon used comprises a first low stretchable section, which is formed by a partial cross-linking treatment and which partially extends, over less than a half of the circumferential region on the balloon, along the axial direction thereof; and a second low stretchable section, which is formed by a partial cross-linking treatment and which partially extends, over less than a half of the circumferential region on the cylindrical balloon, along the axial direction of the balloon; the first and second sections being circumferentially arranged in opposite directions of the balloon and arranged in such a manner that the positions thereof are deviated from one another (or they are not in line with each other) in the axial direction of the balloon. The use of the cylindrical balloon can ensure the achievement of a sufficient tissue-separating function due to the variable bending motions of the balloon.

According to a further aspect of the present invention, there is also provided a medical tube equipped with a balloon, which comprises:

a shaft tube for being inserted into a living body;
a cylindrical balloon, one end of which is liquid-tightly connected to the shaft tube at the tip thereof;
a long tool for medical treatments or for diagnoses, whose tip portion is liquid-tightly connected to the other end of the balloon directly or indirectly; and
a first lumen which is formed within the shaft tube and communicates with the interior of the balloon so that a liquid can pass through the balloon and which accommodates the long tool for medical treatments or for diagnoses;

or a medical tube equipped with a balloon, which comprises:

a shaft tube for being inserted into a living body;
a cylindrical balloon, one end of which is liquid-tightly connected to the shaft tube at the tip thereof;
a long tool for medical treatments or for diagnoses, whose tip portion is liquid-tightly connected to the other end of the balloon directly or indirectly;
a first lumen which is formed within the shaft tube and communicates with the interior of the balloon so that a liquid can pass through the balloon and which accommodates the long tool for medical treatments or for diagnoses; and
at least one second lumen which is formed within the shaft tube and is opened at the periphery of the tip thereof; wherein the cylindrical balloon comprises an area having low extensibility which is partially formed on the peripheral portion of the balloon by a cross-linking treatment.

DESCRIPTION OF THE PREFERRED EMBODIMENTS

In the present invention, examples of materials from which the balloon is formed include various kinds of polymer materials, for instance, various kinds of polyolefins such as polyethylenes such as low density polyethylene, linear low density polyethylene, medium density polyethylene and high density polyethylene; polypropylene and ethylene-propylene copolymer; modified polyolefins such as modified polyethylene and modified polypropylene; ethylene-vinyl acetate copolymer (EVA); ethylene-ethyl acrylate copolymer; soft polyvinyl chloride; silicone (for instance, siloxane) copolymers; fluorine plastics such as polytetrafluoroethylene; various kinds of diene polymers; various kinds of elastomers such as polyamide elastomers and olefinic elastomer; and other various polymeric materials such as natural rubber, polyurethane, silicone, polyisoprene and polyamide. Among these materials, preferably used herein are natural rubber, polyethylene, modified polyethylene, soft polyvinyl chloride and silicone, since they have high flexibility and can easily be cross-linked, with polyethylene and modified polyethylene being more preferred and low density polyethylene being particularly preferred.

In the present invention, these materials may be used alone, but they may also be used in the form of polymer alloys obtained by blending with, as minor components, other resin materials in an amount which does not interfere with the cross-linking of the materials and the extension of the resulting balloon or obtained by copolymerization with such other resin materials. In this respect, the term "polymer alloys" herein used refers to the concept which embraces polymer blends, graft copolymers, block copolymers and random copolymers.

Moreover, materials from which the balloon is formed may likewise include those which can be cross-linked, by nature, when it is irradiated with γ-rays or electron rays and the like or combinations of materials which are hardly cross-linked by nature, with a variety of cross-linking agents. In addition, it is also possible to use a material capable of being easily cross-linked by nature to which a cross-linking agent is additionally added.

In respect of the balloon according to the present invention, a low stretchable section can easily be formed on only a part of the balloon along the circumferential direction thereof by cross-linking the balloon in such a manner that the former has an extent of cross-linking (degree of cross-linking) different from that of the remaining section of the balloon along the circumferential direction thereof, whereby one can secure a sufficient difference between the percentages of elongation of the low and high stretchable sections. Accordingly, the balloon can be bent to a considerable extent by incorporating such a balloon into a medical tube and then injecting a fluid into the balloon. In the balloon of the present invention, the low stretchable section distributed along the circumferential direction of the balloon can be formed without using a material different from that used for forming the remaining section of the balloon. In other words, the whole of the balloon may be formed from a single material and then only a part of the balloon in the circumferential direction thereof is cross-linked. This may eliminate any problem which possibly arises when the balloon is formed from two different materials, for instance, any separation and break of these two materials at the boundary therebetween and accordingly, highly safe balloons can stably be produced.

The cross-linking treatment used in the present invention may, for instance, be the radiation cross-linking method wherein materials such as polyethylene and soft polyvinyl chloride which are susceptible to cross-linking by nature are irradiated with, for instance, high-energy radiations such as electron rays and γ-rays (in particular cases, they also include, for instance, X-rays, β-rays, heavy charged particle beams and neutron beams) and ultraviolet light rays; cross-linking treatments wherein a variety of cross-linking agents are incorporated into polymeric materials and then irradiated with, for instance, high-energy radiations such as electron rays and γ-rays (in particular cases, they also include, for instance, X-rays, β-rays, heavy charged particle beams and neutron beams) and ultraviolet light rays; or cross-linking treatments in which polymeric materials are cross-linked by the application of heat.

The cross-linking agents usable herein may be selected from a wide variety of conventionally known ones which can preferably be combined with plastic materials used. In addition, the cross-linking agents may properly be selected depending on the cross-linking means selected such as cross-linking by irradiation with electron rays, γ-rays and ultraviolet rays and cross-linking by heating. Specific examples of cross-linking agents include organic peroxides such as 2,4-dichlorobenzoyl peroxide, benzoyl peroxide, 1,1-di-(t-butylperoxy)-3,3,5-trimethyl cyclohexane, n-butyl-4,4'-di-(t-butylperoxy)valerate, α,α'-bis(t-butylperoxy diisopropyl) benzene, 2,5-dimethyl-2,5-di-(t-butylperoxy) hexyne-3, di-t-butyl peroxide, 2,5-dimethyl-2,5-di-(t-butylperoxy)hexane, t-butylperoxy cumene and dicumyl peroxide; sulfur atom-containing compounds such as sulfur, sulfur chloride and dithiol; cross-linking agents which can generate radicals through, for instance, thermal decomposition, redox decomposition and ionique decomposition and wherein the resulting radicals pick up hydrogen atoms to thus form crosslinks, such as aminoazobenzene, quinone and polynitrobenzene; or various kinds of acrylates, methacrylates or triesters such as β-acryloyloxyethyl hydrogen succinate, lauryl acrylate, ethylene glycol dimethacrylate, diethylene glycol dimethacrylate, triethylene glycol dimethacrylate, polyethylene glycol dimethacrylate, 1,3-butylene glycol dimethacrylate, 1,6-hexanediol dimethacrylate, neopentyl glycol dimethacrylate, polypropylene glycol diacrylate, 2,2 -bis[4-(acryloxy diethoxy)phenyl]propane, 2-hydroxy-1-acryloxy-3 -methacryloxy propane, trimethylolpropane trimethacrylate, trimethylolpropane triacrylate, tetramethylolmethane triacrylate, tetramethylolmethane tetraacrylate, ditrimethylolpropane tetraacrylate, di(meth)acrylate, trimethacrylate and tetra(meth) acrylate.

When using such a cross-linking agent, a balloon which comprises sections, distributed along the circumferential direction thereof, having a content of a cross-linking agent higher than that in the remaining sections is formed by, for instance, extrusion molding or blow molding using a combination of a cross-linking agent-containing resin and a resin free of any cross-linking agent, or a combination of a resin having a relatively high content of a cross-linking agent and a resin having a relatively low content thereof and then the balloon is irradiated with the foregoing electron rays or ultraviolet rays or heat is applied thereto to thus induce a difference in physical properties between the sections formed from the foregoing two kinds of resins. In this case, the dose of, for instance, ultraviolet rays for irradiation or the quantity of heat to be applied to the balloon may be uniform over the whole balloon in the circumferential direction or may be selected such that the section having a higher content of the cross-linking agent is irradiated or heated to a higher extent as compared with the remaining sections. In case where the cross-linking agent is only partially added to the balloon along its circumferential direction, only the corresponding sections may be irradiated with radiant rays or heated to form crosslinks or control the physical properties of the sections.

In case where a cross-linking agent is incorporated into a starting resin, the resin containing the cross-linking agent may be different from that free of any cross-linking agent (or that containing it in a small amount), but these resins are preferably identical or similar to one another (same polymer group, for instance, polyamide and polyamide elastomer, and as other combination, PET and polyester elastomer). In addition, these resins are preferably compatible with one another and, in this sense, combinations of the same kind of polymer materials are preferably used in the present invention.

Among the foregoing cross-linking treatments, the simplest is to form crosslinks by the radiation cross-linking. This method permits the precise control of the positions and shapes of the low stretchable section formed on the balloon by the use of an appropriate mask (or a barrier material) in a uniform radiation field and thus the low stretchable section can be formed in various embodiments such as an embodiment in which the section extends along the axial direction, an embodiment in which a first low stretchable section and a second low stretchable section are present on the opposite sides along the circumferential direction of a cylindrical balloon and they are not in line with each other in the axial direction of the balloon, an embodiment wherein the section helically extends along the axial direction of the balloon, an embodiment wherein the section obliquely extends with respect to the axial direction of the balloon or a pattern wherein at least three sections are alternately arranged along the circumferential direction of the balloon.

The balloon for medical tubes and the medical tube equipped with such a balloon according to the present invention will be described in more detail below, with reference to the embodiments as shown in the attached figures.

Figure 1:
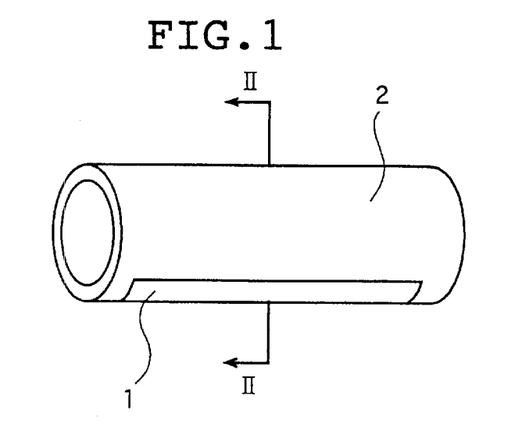
FIG. 1 is a perspective diagram showing an embodiment of the balloon for medical tubes according to the present invention.
Figure 2:
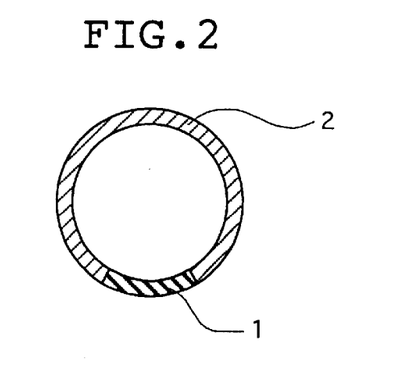
FIG. 2 is a cross sectional view taken along the line II—II in FIG. 1.

FIG. 1 is a perspective diagram showing the balloon for medical tubes according to a first embodiment of the present invention and FIG. 2 is a cross sectional view taken along the line II—II in FIG. 1. As will be seen from FIGS. 1 and 2, the balloon for medical tubes according to the first embodiment of the present invention comprises a relatively low stretchable section 1 which is formed by a selective cross-linking treatment and a relatively high stretchable section 2 and the relatively low stretchable section 1 extends, over less than a half of the circumferential region on the cylindrical balloon, along the axial direction of the balloon, respectively.

Figure 3:
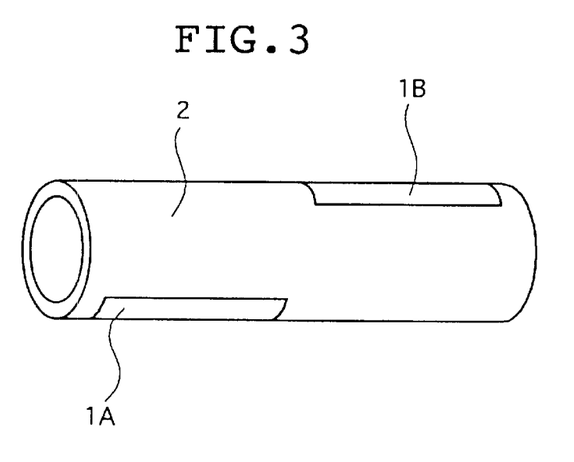
FIG. 3 is a perspective diagram showing another embodiment of the balloon for medical tubes according to the present invention.

FIG. 3 is a perspective diagram showing the balloon for medical tubes according to another embodiment of the present invention, the balloon as shown in this figure comprises first and second relatively low stretchable sections 1A and 1B which are formed by a selective cross-linking treatment and a relatively high stretchable section 2, the first low stretchable section 1A partially extends over less than a half, for instance, about half of the circumferential region on the cylindrical balloon, along the axial direction of the balloon, while the second low stretchable section 1B partially extends over less than a half, for instance, about half of the circumferential region on the cylindrical balloon, along the axial direction of the balloon, the sections 1A and 1B are present on the opposite sides of the balloon respectively and they are deviated from one another in the axial direction of the balloon, preferably they substantially do not overlap with each other in the axial direction of the balloon.

In the foregoing low stretchable sections 1, 1A, 1B, the stretchability may continuously or stepwise be changed between neighboring sections distributed along the circumferential direction of the balloon and the rate of the low stretchable section 1, 1A, 1B with respect to the whole circumferential area of the balloon is preferably not more than 30% and more preferably not more than 10%. In addition, the low stretchable section 1, 1A, 1B may extend over only a part of the length on the balloon in the axial direction or may continuously or intermittently extend over the entire length thereof, depending on the desired degree of bending and the curved shape of the balloon observed when using a medical tube equipped with such a balloon.

A cylindrical balloon including two low stretchable sections is shown in FIG. 3, but a cylindrical balloon comprising at least three such low stretchable sections may likewise be used in the present invention. For instance, when the balloon comprises three such sections, the first low stretchable section extends over a part of the circumferential direction of the balloon and over about ⅓ time the length of the balloon in the axial direction, the second low stretchable section extends over a part of the circumferential direction of the balloon and over about ⅓ time the length of the balloon in the axial direction and the third low stretchable section extends over a part of the circumferential direction of the balloon and over about ⅓ time the length of the balloon in the axial direction. In this case, the three low stretchable sections may be arranged as follows: the first and second sections are present on the opposite sides of the balloon in the circumferential direction, while the first and third sections are present on the same side of the balloon in the circumferential direction, and these three sections are distributed on the side of the balloon in such a manner that they are not in line with each other in the axial direction of the balloon.

The difference in stretchability can be imparted to the balloon by appropriately changing mechanical properties such as the rate of drawing, elasticity modulus, rigidity and hardness of the material constituting the balloon, or physical properties such as the thickness of the balloon to thus establish a difference in each value between sections on the balloon, but the cross-linking treatment is the simplest method for establishing such a difference and the position and the shape of the low stretchable section 1, 1A, 1B formed on the balloon can precisely be controlled. Therefore, the balloon of the present invention is limited to a cylindrical balloon for medical tubes, which is equipped with low stretchable sections formed by a cross-linking method.

The cross-linking treatment used in the invention will hereinafter be explained in more detail while taking, as an example, the case where a balloon having a partial difference in the stretchability is formed by selectively establishing a difference in the stretchability by the electron radiation cross-linking. For instance, a balloon is formed using a low density polyethylene and the stretchability thereof is changed by changing the dose of electron rays, i.e., the degree of cross-linking along the circumferential direction. Preferably, the high stretchable section 2 formed on the balloon is irradiated with electron rays at a dose ranging from 5 to 35 Mrad, while the low stretchable section 1, 1A, 1B is irradiated with electron rays at a dose of 3 to 10 Mrad higher than that used for the irradiation of the high stretchable section. More preferably, the high stretchable section 2 is irradiated with electron rays at a dose ranging from 20 to 25 Mrad, while the latter is irradiated with electron rays at a dose of 3 to 5 Mrad higher than that used for the irradiation of the former.

Figure 4:
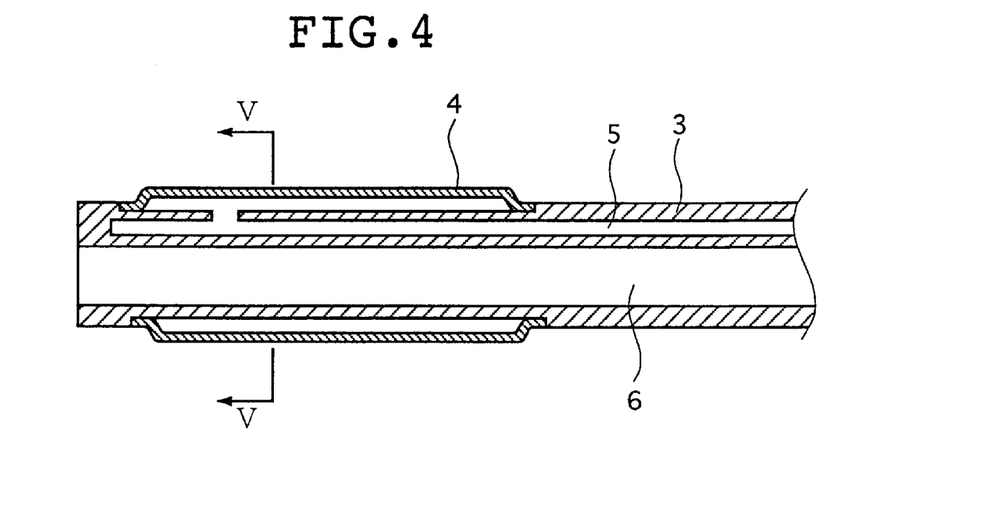
FIG. 4 is a cross sectional view showing a part of a first embodiment of the medical tube equipped with a balloon according to the present invention.
Figure 5:
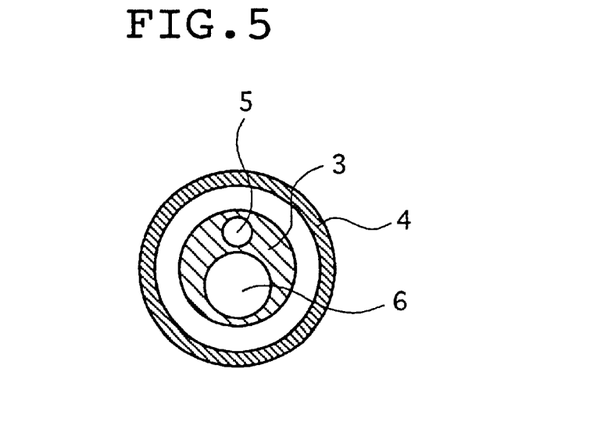
FIG. 5 is a cross sectional view taken along the line V—V in FIG. 4.

FIG. 4 is a cross sectional view showing a part of a first embodiment of the medical tube equipped with a balloon according to the present invention and FIG. 5 is a cross sectional view taken along the line V—V in FIG. 4. As will be seen from FIGS. 4 and 5, the medical tube according to the first embodiment of the present invention comprises a shaft tube 3 for being inserted into a living body and a cylindrical balloon 4 which is liquid-tightly connected to the shaft tube 3 at the periphery of the tip thereof. Furthermore, a first lumen 5 is provided within the shaft tube 3 and communicates with the interior of the balloon 4 and at least one second lumen 6 is provided within the shaft tube 3 and is opened at the tip of the tube. In this embodiment of the present invention, the cylindrical balloon 4 has a particular shape and specific properties as has been described above in connection with FIGS. 1 and 2 or FIG. 3.

The foregoing shaft tube 3 is constituted by, for instance, a polymeric material having a certain degree of flexibility, such as polyethylene, polyethylene terephthalate, soft polyvinyl chloride, polypropylene, polyurethane, polyamide, polyimide, polytetrafluoroethylene, silicone rubber or ethylene-vinyl acetate copolymer.

Moreover, the outer surface of the shaft tube 3 and the balloon 4 may be coated with a low-frictional material such as a hydrophilic polymer (e.g., maleic anhydride copolymer) or a fluorine-containing resin (e.g., polytetrafluoroethylene) in order to reduce the friction between the tube and the balloon and a body cavity encountered when the medical tube is inserted into the body cavity.

In the medical tube according to the first embodiment of the present invention, a tubular reinforcing material is preferably embedded in the shaft tube 3 in the proximity of the periphery thereof over a part or the whole length of the tube 3 so as to surround each lumen 5, 6. Examples of the reinforcing material include those produced from metallic materials such as stainless steel and superelastic alloys; those produced from resin materials such as polyamide, polyethylene, polypropylene, polyester, polyimide and ABS resins; and those constituted by filament-like bodies of, for instance, carbon fibers, with braided bodies obtained by crossing such filament-like bodies each other in the form of a braid being particularly preferred. The incorporation of such a reinforcing material permits an increase in the torsional rigidity of the shaft tube 3 and this in turn ensures the effective transfer, to the tip of the shaft tube, of the rotatory power generated when the tube is rotated at the base end thereof, i.e., the improvement of the torque-transfer characteristics of the tube. Moreover, the use of such a reinforcing material also inhibits and obstruction or stenosis of the lumen 5, 6 even when the shaft tube 3 is bent, in particular, at a sharp angle.

In addition, the X-ray radiogpaque property is preferably imparted to the shaft tube 3 so that the position of the shaft tube 3 can be confirmed by the radioscopy, when it is inserted into a living body. Examples of the method for imparting the susceptibility to the X-ray radiography include those comprising the step of incorporating, into the material for the shaft tube 3, a radiopaque substance such as barium sulfate, bismuth oxide or tungsten and those comprising the step of embedding a marker comprising such a radiopaque substance in a predetermined position on the tube 3 or adhering such a marker to the surface thereof.

In the medical tube according to the first embodiment of the present invention, a pressure can be applied to the first lumen 5 which communicates with the interior of the balloon by connecting it to a pressing fluid source through a fluid pressure controller; by connecting it to a pressing fluid source through a fluid pressure controller capable of applying a pulsatile pressure; or by applying a pulsatile pressure to the balloon using a pulsating pump for generating pulsatile pressure. The pressing fluid may be a gas or a liquid. The fluid pressure controller can adjust the pressure, to be applied to the balloon, to the range of preferably from 0 to 15 atm and the pulse frequency of the pressure when it is applied to the balloon in a series of pulses ranges from 1 to 20 Hz and the minimum and maximum levels of the pulsatile pressure applied to the balloon are 0 atm and 1~5 atm, respectively. The angle of bending or that of S-shaped bending varies arbitrarily or in any series of pulses in response to the applied pressure or the pressure variation and the balloon is in general bent at an angle ranging from 0 to 90 deg. Furthermore, the application of a pulse-like pressure gives rise to, for instance, S-shaped bending motions. It is preferred that the balloon does not undergo any S-shaped bending form when the minimum pulse-like pressure is applied, but it is bent in an S-shaped form when the maximum pulse-like pressure is applied. The pulse frequency of the pressure applied to the balloon varies depending on the energy required for the separation of biological tissues, but preferably it in general falls within the range of from 1 to 20 Hz. The fluid pressure controller may be adjusted manually or electrically.

As has been discussed above, the medical tube of the present invention comprises the relatively low stretchable section and the relatively high stretchable section and accordingly, if a fluid pressure is applied to the balloon, the balloon undergoes bending towards the side of the relatively low stretchable section and the shaft tube is also bent in response thereto. In other words, the extent of the bending can continuously be changed in proportion to the applied fluid pressure. The shape of the bent balloon is changed depending on the shape and arrangement, on the balloon, of the relatively low stretchable section(s). Therefore, the balloon permits appropriate selection of branchings of the biological tubular cavities and the medical tube can be forced even in tissues other than the biological tubular cavities while appropriately selecting the course of progress. In addition, the direction of the opening at the tip of the shaft tube can also be changed continuously by bending the shaft tube and accordingly, the site to be examined or treated can precisely be specified.

In the medical tube according to the first embodiment of the present invention, at least one second lumen 6 which is opened at the tip of the shaft tube may serve as a channel through which a guide wire, tools for medical treatments or diagnoses, or the like can be inserted. Examples of such tools for medical treatments or diagnoses are endoscopes, forceps, a variety of treatment tools, brushes for cytologic examination, needles, probes (for use in, for instance, lithocenosis, laser ray-irradiation and abrasion) emitting or generating high-frequency waves, ultrasonics and hydraulic impulse waves; and a variety of sensors and leading wires therefor.

Figure 6:
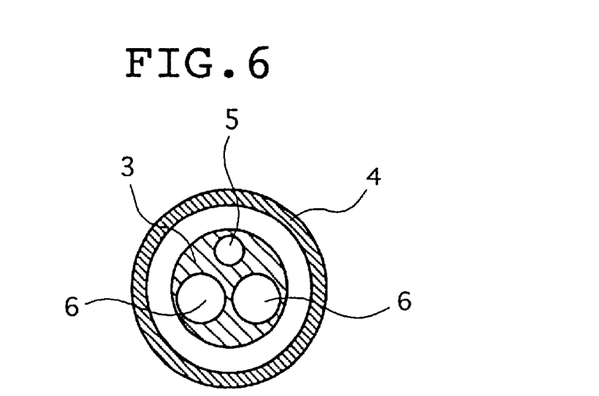
FIG. 6 is a cross sectional view showing another example of the first embodiment of the medical tube equipped with a balloon according to the present invention.

Moreover, the medical tube of the present invention permits the injection of a fluid into biological tissues or tubular organs or the suction of a fluid, through the space formed between the tools for medical treatments or diagnoses and the wall of the lumen, or through another second lumen 6. More specifically, the medical tube is inserted into a living body to thus administer, for instance, a medical fluid into indwelling biological tissues and tubular organs, or the tube is used as a flush channel for injecting a transparent liquid (such as physiological saline and a glucose injection) used for forcing out a body fluid such as the blood or the bile which obstruct the view when observing biological tissues or tubular organs with an endoscope.

The medical tube shown in FIGS. 4 and 5 comprises a single second lumen 6, but the medical tube according to the present invention may be equipped with two or more second lumens 6 as shown in FIG. 6 depending on the applications thereof. Such a shaft tube provided with multiple lumens and the method for producing the same are known from the prior art.

Figure 7:
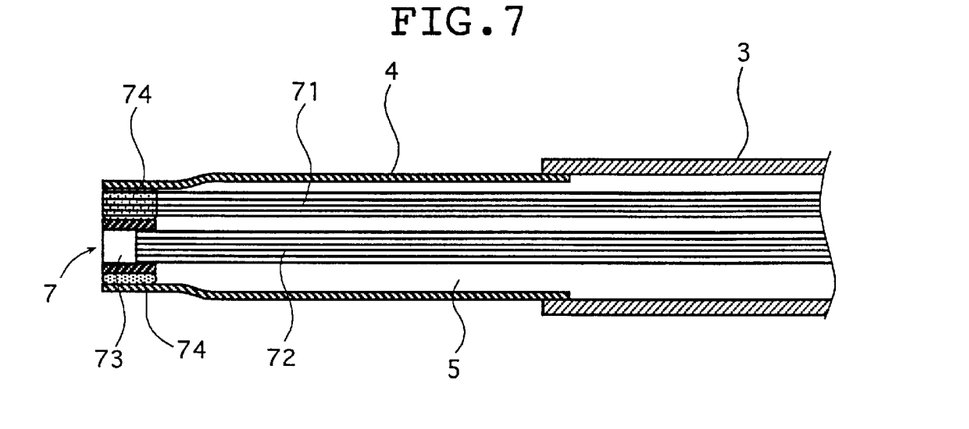
FIG. 7 is a cross sectional view showing a part of a second embodiment of the medical tube equipped with a balloon according to the present invention.

FIG. 7 is a cross sectional view showing a part of the medical tube according to a second embodiment of the present invention. The medical tube according to a second embodiment of the present invention comprises a shaft tube 3 which is inserted into a living body; a cylindrical balloon 4 liquid-tightly connected to the shaft tube 3 at the one end thereof; and a long tool 7 for medical treatments or diagnoses whose tip portion is directly or indirectly connected to the other end of the cylindrical balloon in a liquid-tight manner. A first lumen 5 which is provided within the shaft tube 3 and communicates with the interior of the balloon to thus allow the passage of a fluid therethrough and the long tool 7 for medical treatments or diagnoses are accommodated in the first lumen 5. In this embodiment of the present invention, the cylindrical balloon 4 has a particular shape and specific properties as has been described above in connection with FIGS. 1 and 2 or FIG. 3.

Examples of such tools 7 for medical treatments or diagnoses are endoscopes, forceps, a variety of treatment tools, brushes for cytologic examination, probes (for use in, for instance, lithocenosis, laser ray-irradiation and abrasion) emitting or generating high-frequency waves, ultrasonics and hydraulic impulse waves; and a variety of sensors and leading wires therefor.

In the medical tube according to the second embodiment of the present invention, the long tool 7 for medical treatments or diagnoses may be connected to the cylindrical balloon 4 by directly connecting these members, by indirectly connecting them through another tube or by indirectly connecting them through another tube which is laid across these members.

The embodiment shown in FIG. 7 relates to an example in which an endoscope for observing biological tissues or the interior of tubular organs is incorporated into the medical tube as the tool 7 for medical treatments or diagnoses. The endoscope comprises a light-transmitting fiber bundle 71 (light-guiding fiber bundle), a light-receiving fiber bundle 72 (image fiber bundle) and a lens 73 fitted to the tip of the light-receiving fiber bundle 72. The tip of the light-transmitting fiber bundle 71 extends over the lens 73 and arrives at the tip of the medical tube. Then the other end (tip) of the cylindrical balloon 4 is liquid-tightly connected to the light-transmitting fiber bundle 71 and the lens 73 by an adhesive 74.

The medical tube according to the second embodiment of the present invention is free of any lumen which is opened at the tip of the shaft tube and therefore, this embodiment does not permit the injection of a fluid into biological tissues or the interior of tubular organs or the suction of a fluid therefrom. As has been explained above in connection with the medical tube equipped with the balloon as shown in FIG. 4, however, the angle of bending and the shape of the bent balloon or the medical tube can arbitrarily be changed in proportion to the controlled pressure of the fluid pressure controller if the first lumen 5, which communicates with the interior of the balloon 4, is connected to the source of a pressing fluid through the fluid pressure controller, when practically using the medical tube, and the extent of the bending can continuously be changed in response to the fluid pressure. For this reason, the medical tube allows the tool for medical treatments or disgnoses to proceed to a desired direction. For instance, when the medical tube having a built-in endoscope is forced in a biological tubular cavity, the branching through which the tube may advance can appropriately be selected while observing and confirming with the endoscope to thus be able to precisely specify the site to be examined. Moreover, the medical tube has a quite simple structure and the diameter thereof can be made very small.

In the medical tube according to the second embodiment of the present invention, the angle of bending of the bent balloon or the medical tube can arbitrarily be changed in proportion to the controlled pressure applied by the fluid pressure controller and the pulse-like pressure-generating pulsatile pump if the first lumen 5, which communicates with the interior of the balloon 4, is connected to the source of a pressing fluid through the fluid pressure controller and to the pulse-like pressure-generating pulsatile pump, when practically using the medical tube, and the extent of the bending can continuously be changed in response to the fluid pressure and the pulsatile pressure, as has been explained above in connection with the medical tube shown in FIGS. 4 and 5. Accordingly, the balloon can guide the medical tube towards a desired direction, while separating biological tissues and observing and confirming them with the endoscope. Moreover, the medical tube has a quite simple structure and the diameter thereof can be made very small.

Figure 8:
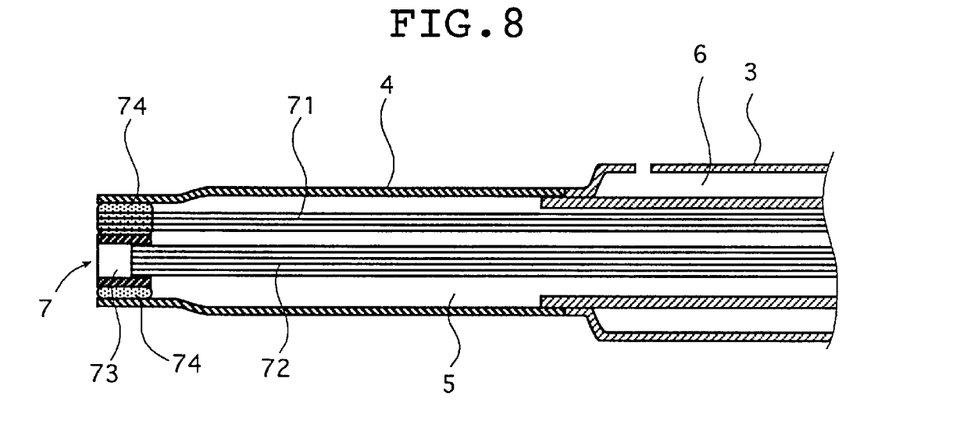
FIG. 8 is a cross sectional view showing a part of a third embodiment of the medical tube equipped with a balloon according to the present invention.
Figure 9:
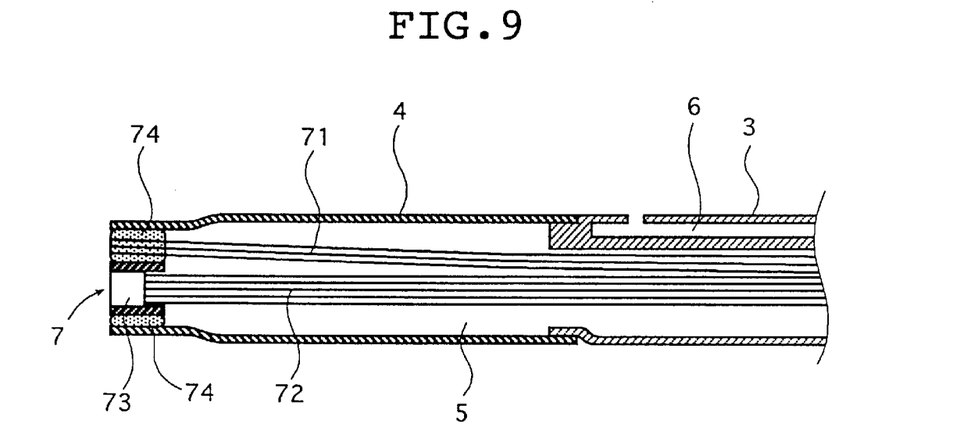
FIG. 9 is a cross sectional view showing another example of the third embodiment of the medical tube equipped with a balloon according to the present invention.

FIGS. 8 and 9 each is a cross sectional view showing a part of the medical tube according to a third embodiment of the present invention. The medical tube according to the third embodiment of the present invention comprises a shaft tube 3 which is inserted into a living body; a cylindrical balloon 4 whose one end is liquid-tightly connected to the tip of the shaft tube 3; and a long tool 7 for medical treatments or diagnoses, whose tip portion is directly or indirectly connected, liquid-tightly, to the other end of the cylindrical balloon 4. A first lumen 5 is formed within the shaft tube 3 and communicates with the interior of the balloon 4 so that a fluid can pass therethrough and at least one second lumen 6 is also formed within the shaft tube 3 and is opened at the periphery of the tip thereof. In addition, the long tool 7 for medical treatments or diagnoses is accommodated in the first lumen 5.

The long tool 7 for medical treatments or diagnoses is identical to those described above in connection with the medical tube according to the second embodiment of the present invention and the tool 7 can likewise be connected to the cylindrical balloon 4 by the same methods explained above. FIGS. 8 and 9 also show an embodiment having a built-in endoscope for observing biological tissues or the interior of the tubular organs, as the tool 7 for medical treatments or diagnoses and the endoscope is also identical to that explained above.

The medical tube according to the third embodiment of the present invention comprises the lumen which is opened at the periphery of the tip of the shaft tube 3 and therefore, the tube permits the injection of a fluid into biological tissues or tubular organs or the suction of a fluid therefrom. Moreover, the angle of bending and the shape of the bent balloon or the medical tube provided with the balloon can arbitrarily be changed in proportion to the controlled pressure of the fluid pressure controller if the first lumen 5, which communicates with the interior of the balloon 4, is connected to the source of a pressing fluid through the fluid pressure controller, when practically using the medical tube, as has been explained above in connection with the medical tube equipped with the balloon as shown in FIG. 4 and the extent of the bending can continuously be changed in response to the fluid pressure. For this reason, the medical tube allows the tool for medical treatments or disgnoses to proceed to a desired direction. For instance, when the medical tube having a built-in endoscope is forced in a biological tubular cavity, the branching through which the tube can advance towards a desired site can appropriately be selected while observing and confirming with the endoscope to thus be able to precisely specify the site to be examined. Moreover, the medical tube has a quite simple structure and the diameter thereof can be made very small.

In the medical tube according to the third embodiment of the present invention, the angle of bending of the bent balloon or medical tube can arbitrarily be changed in proportion to the controlled pressure applied by the fluid pressure controller and the pulse-like pressure-generating pulsatile pump if the first lumen 5, which communicates with the interior of the balloon 4, is connected to the source of a pressing fluid through the fluid pressure controller and to the pulse-like pressure-generating pulsatile pump, when practically using the medical tube, and the extent of the bending can continuously be changed in response to the fluid pressure and the pulse-like pressure, as has been explained above in connection with the medical tube shown in FIGS. 4 and 5. Accordingly, one can precisely specify the direction along which the medical tube should be forced into biological tissues while separating the biological tissues and observing and confirming the condition with the endoscope. Moreover, the medical tube has a quite simple structure and the diameter thereof can be made very small.

Figure 10:
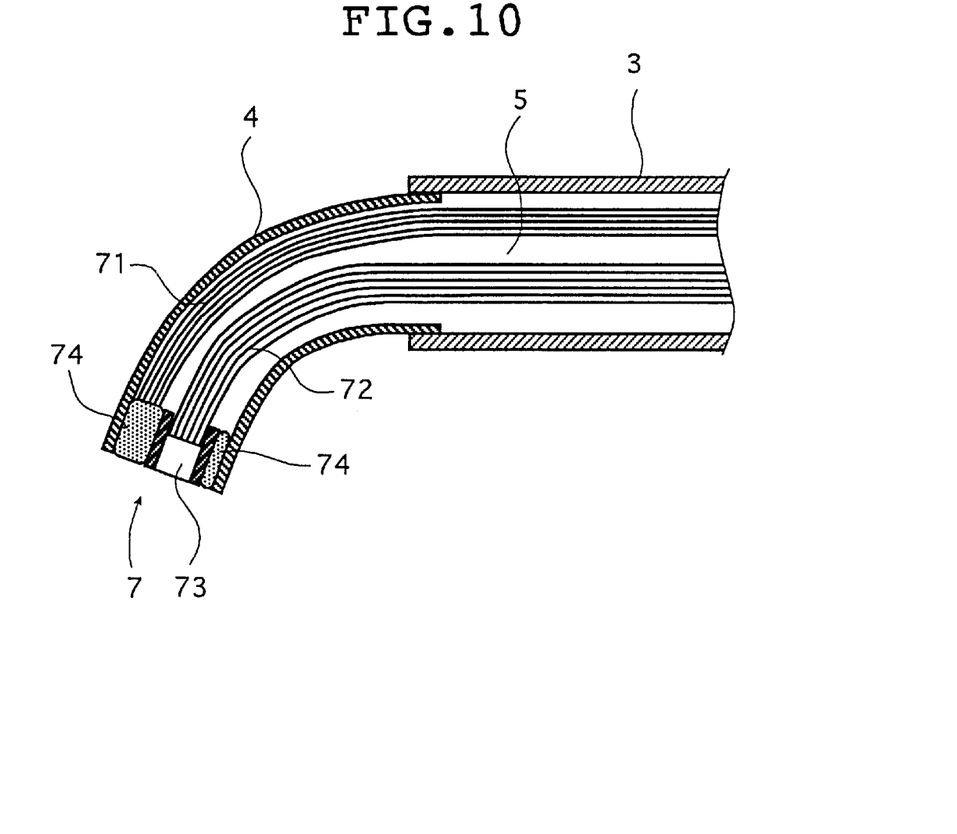
FIG. 10 is a cross sectional view showing the balloon, in its bent state, of the medical tube equipped with a balloon shown in FIG. 7.

FIG. 10 shows the balloon 4 of the medical tube, as shown in FIG. 7, equipped with a balloon shown in FIG. 1, in its bent state, and more specifically, the balloon which is bent toward the side of the relatively low stretchable section by connecting the first lumen 5 communicating with the interior of the balloon 4 to the fluid pressure source through the fluid pressure controller and injecting a fluid into the balloon 4. The extent of the bending can continuously be changed in response to the magnitude of the fluid pressure.

Figure 11:
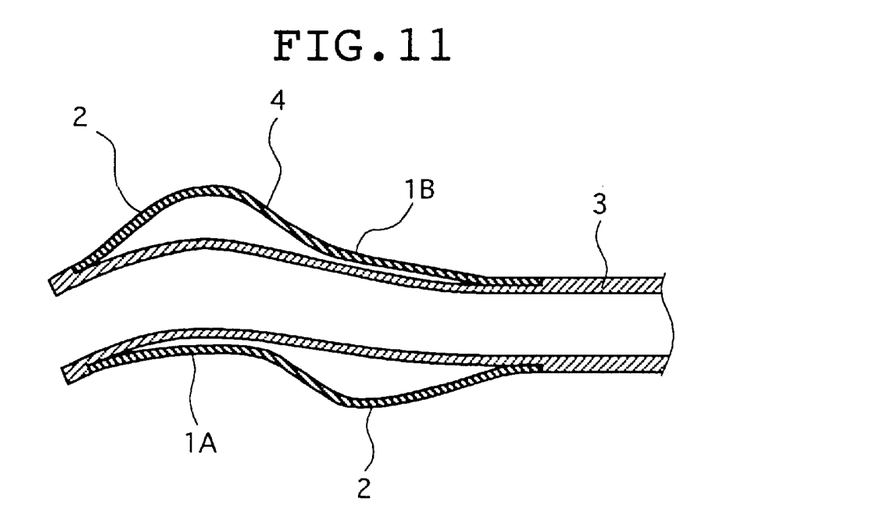
FIG. 11 is a cross sectional view showing the balloon, in its S-shaped bent state, of the medical tube equipped with a balloon shown in FIG. 3.

FIG. 11 shows the balloon 4 of the medical tube equipped with a balloon shown in FIG. 4, which is bent in an S-shaped form, and more specifically, the balloon 4 which is bent in an S-shaped form toward the side of the relatively low stretchable section by connecting the first lumen 5 communicating with the interior of the balloon 4 to the fluid pressure source through the fluid pressure controller and injecting a fluid into the balloon 4; or by connecting the lumen 5 to the pulse-like pressure-generating pulsatile pump and injecting a fluid into the balloon 4 in a series of pulses. The extent of the bending can continuously be changed in response to the magnitude of the fluid pressure.

The balloon for medical tubes according to the present invention as well as applications thereof have been described above in detail with reference to the embodiments shown in the accompanying drawings, but the present invention is not restricted to these specific ones at all.

As has been discussed above in detail, the medical tube of the present invention does not require the use of any complicated structure and the diameter thereof can be made small. Moreover, the bending angle of the tip thereof is greatly affected by the fluid pressure applied and therefore, the angle can freely be changed by controlling the pressure. Thus, the present invention can provide a medical tube having a variable bending ability and hence a direction-selecting function, one can thus positively approach the medical tube to a desired site in biological tissues by appropriately adjusting the bending angle of the balloon and the present invention can also provide a medical tube structure having an ability of variable bending motions and an ability of separating biological tissues.

What is claimed is:

1. A medical tube equipped with a balloon comprising:
   a shaft tube for being inserted into a living body, the shaft having a tip possessing a periphery;
   a cylindrical balloon connected in a liquid-tight manner to the shaft tube at the periphery of the tip of the shaft tube, the balloon having an interior;
   a first lumen which is formed within the shaft tube and which communicates with the interior of the balloon; and
   at least one second lumen which is formed within the shaft tube and which is opened at the tip of the shaft tube;
   wherein the cylindrical balloon comprises at least one low stretchable section formed on a circumferential region on the balloon by a partial cross-linking treatment and arranged such that upon introducing pressurized fluid into the cylindrical balloon, the cylindrical balloon bends toward a side of the low stretchable section of the cylindrical balloon.

2. The medical tube equipped with a balloon as set forth in claim 1, wherein the at least one low stretchable section does not cause bending of the balloon in the absence of the pressurized fluid being injected into the interior of the balloon.

3. The medical tube equipped with a balloon as set forth in claim 1, wherein the cylindrical balloon comprises the at least one relatively low stretchable section which is partially formed on a circumferential region on the balloon and a relatively high stretchable section, and both the relatively low stretchable section and the relatively high stretchable section are formed by a cross-linking treatment and a difference in stretchability between the sections is established by changing a degree of the cross-linking.

4. The medical tube equipped with a balloon as set forth in claim 1 wherein the at least one low stretchable section comprises a first low stretchable section which partially extends over less than half of the circumferential region on the cylindrical balloon, along an axial direction of the balloon; and the cylindrical balloon comprising a second low stretchable section formed by a cross-linking treatment, which partially extends over less than a half of the circumferential region on the cylindrical balloon, along the axial direction of the balloon, wherein the first and second sections are circumferentially arranged in opposite directions on the balloon and are arranged so that they are not in line with each other in the axial direction of the balloon.

5. The medical tube equipped with a balloon as set forth in claim 1, wherein the cylindrical balloon comprises the at least one relatively low stretchable section formed by a selective cross-linking treatment and a relatively high stretchable section, the relatively low stretchable section existing only within a half portion of a circumferential area on the cylindrical balloon, with a remaining half portion of the circumferential area on the cylindrical balloon consists of the relatively high stretchable section.

6. The medical tube equipped with a balloon as set forth in claim 5, wherein the relatively high stretchable section has an extent of cross-linking different from that of the relatively low stretchable section.

7. The medical tube equipped with a balloon as set forth in claim 5, wherein the cylindrical balloon consists essentially of a single relatively low stretchable section formed by a selective cross-linking treatment and a relatively high stretchable section.

8. The medical tube equipped with a balloon as set forth in claim 1, wherein the at least one low stretchable section is a first low stretchable section arranged only on a portion less than a half of a circumferential area on the cylindrical balloon, the first low stretchable section extending partially along an axial direction of the cylindrical balloon, and a second low stretchable section formed by a cross-linking treatment and arranged only on a portion less than a half of the circumferential area on the cylindrical balloon, the second low stretchable section extending partially along the axial direction of the cylindrical balloon, and the first and second sections being circumferentially arranged in opposite directions on the balloon and being arranged so that they do not overlap each other in the axial direction of the balloon.

9. The medical tube equipped with a balloon as set forth in claim 8, wherein the first and second sections do not overlap each other in the circumferential direction of the balloon.

10. The medical tube equipped with a balloon as set forth in claim 1, wherein the cylindrical balloon possesses a circumference, the at least one low stretchable section constituting a relatively low stretchable section, the cylindrical balloon comprising a relatively high stretchable section possessing a higher stretchability than the relatively low stretchable section, said relatively low stretchable section extending along an axial direction of the cylindrical balloon as well as circumferentially over only a portion less than half the circumference of the cylindrical balloon, said relatively low stretchable section and said relatively high stretchable section being positioned relative to one another such that upon introducing pressurized fluid into the cylindrical balloon, the cylindrical balloon bends toward a side of the relatively low stretchable section of the cylindrical balloon by virtue of the balloon expanding to a greater extent over the relatively high stretchable section and to a lesser extent over the relatively low stretchable section.

11. The medical tube equipped with a balloon as set forth in claim 10, wherein the relatively low stretchable section is a first relatively low stretchable section, and including a second relatively low stretchable section that is less stretchable than the relatively high stretchable section, the first and second relatively low stretchable sections being positioned in non-axially overlapping positions with respect to one another.

12. The medical tube equipped with a balloon as set forth in claim 10, wherein the relatively low stretchable section is a first relatively low stretchable section, and including a second relatively low stretchable section that is less stretchable than the relatively high stretchable section, the first and second relatively low stretchable sections being positioned at oppositely located circumferential portions of the cylindrical balloon.

13. A medical tube equipped with a balloon comprising:
a shaft tube for being inserted into a living body, the shaft tube having a tip;
a cylindrical balloon having one end connected in a liquid-tight manner to a tip of the shaft tube, the balloon having an interior;
a long tool for medical treatments or for diagnoses, the tool having a tip portion connected in a liquid-tight manner to an opposite end of the balloon directly or indirectly; and
a first lumen formed within the shaft tube and communicating with the interior of the balloon so that a liquid can pass through the balloon, the first lumen accommodating the long tool for medical treatments or for diagnoses;
wherein the cylindrical balloon comprises a low stretchable section which is partially formed on a circumferential region on the balloon by a cross-linking treatment and arranged such that upon introducing pressurized fluid into the cylindrical balloon, the cylindrical balloon bends toward a side of the low stretchable section of the cylindrical balloon.

14. The medical tube equipped with a balloon as set forth in claim 13, wherein the low stretchable section does not cause bending of the balloon in the absence of the pressurized fluid being injected into the interior of the balloon.

15. The medical tube equipped with a balloon as set forth in claim 13, wherein the cylindrical balloon comprises the at least one relatively low stretchable section which is partially formed on a circumferential region on the balloon and a relatively high stretchable section, and both the relatively low stretchable section and the relatively high stretchable section are formed by a cross-linking treatment and a difference in stretchability between the sections is established by changing a degree of the cross-linking.

16. The medical tube equipped with a balloon as set forth in claim 13 further comprising at least one second lumen formed within the shaft tube and opening at a periphery on the tip of the shaft tube.

17. The medical tube equipped with a balloon as set forth in claim 13, wherein the cylindrical balloon comprises the at least one relatively low stretchable section formed by a selective cross-linking treatment and a relatively high stretchable section, the relatively low stretchable section existing only within a half portion of a circumferential area on the cylindrical balloon, with a remaining half portion of the circumferential area on the cylindrical balloon consists of the relatively high stretchable section.

18. The medical tube equipped with a balloon as set forth in claim 17, wherein the relatively high stretchable section has an extent of cross-linking different from that of the relatively low stretchable section.

19. The medical tube equipped with a balloon as set forth in claim 17, wherein the cylindrical balloon consists essentially of a single relatively low stretchable section formed by a selective cross-linking treatment and a relatively high stretchable section.

20. The medical tube equipped with a balloon as set forth in claim 13, wherein the at least one low stretchable section is a first low stretchable section arranged only on a portion less than a half of a circumferential area on the cylindrical balloon, the first low stretchable section extending partially along an axial direction of the cylindrical balloon, and a second low stretchable section formed by a cross-linking treatment and arranged only on a portion less than a half of the circumferential area on the cylindrical balloon, the second low stretchable section extending partially along the axial direction of the cylindrical balloon, and the first and second sections being circumferentially arranged in opposite directions on the balloon and being arranged so that they do not overlap each other in the axial direction of the balloon.

21. The medical tube equipped with a balloon as set forth in claim 20, wherein the first and second sections do not overlap each other in the circumferential direction of the balloon.

22. The medical tube equipped with a balloon as set forth in claim 13, wherein the cylindrical balloon possesses a circumference, the at least one low stretchable section constituting a relatively low stretchable section, the cylindrical balloon comprising a relatively high stretchable section possessing a higher stretchability than the relatively low stretchable section, said relatively low stretchable section extending along an axial direction of the cylindrical balloon as well as circumferentially over only a portion less than half the circumference of the cylindrical balloon, said relatively low stretchable section and said relatively high stretchable section being positioned relative to one another such that upon introducing pressurized fluid into the cylindrical balloon, the cylindrical balloon bends toward a side of the relatively low stretchable section of the cylindrical balloon by virtue of the balloon expanding to a greater extent over the relatively high stretchable section and to a lesser extent over the relatively low stretchable section.

23. The medical tube equipped with a balloon as set forth in claim 22, wherein the relatively low stretchable section is a first relatively low stretchable section, and including a second relatively low stretchable section that is less stretchable than the relatively high stretchable section, the first and second relatively low stretchable sections being positioned in non-axially overlapping positions with respect to one another.

24. The medical tube equipped with a balloon as set forth in claim 22, wherein the relatively low stretchable section is a first relatively low stretchable section, and including a second relatively low stretchable section that is less stretchable than the relatively high stretchable section, the first and second relatively low stretchable sections being positioned at oppositely located circumferential portions of the cylindrical balloon.

* * * * *